US005776943A

United States Patent [19]
Christians et al.

[11] Patent Number: 5,776,943
[45] Date of Patent: Jul. 7, 1998

[54] RAPAMYCIN METABOLITES

[75] Inventors: Uwe Christians, Langelsheim; Karl F. Sewing; Martin Sattler, both of Hanover, all of Germany

[73] Assignee: American Home Products Corporation, Madison, N.J.

[21] Appl. No.: 699,505

[22] Filed: May 14, 1991

[51] Int. Cl.$^6$ .................. A61K 31/44; C07D 491/00
[52] U.S. Cl. ................................. 514/291; 546/90
[58] Field of Search ..................... 546/90; 514/291

[56] References Cited

U.S. PATENT DOCUMENTS

| 3,929,992 | 12/1975 | Sehgal et al. | 424/122 |
|---|---|---|---|
| 3,993,749 | 11/1976 | Sehgal et al. | 424/122 |
| 4,316,885 | 2/1982 | Rakhit | 424/622 |
| 4,401,653 | 8/1983 | Buckwalter | 514/605 |
| 4,650,803 | 3/1987 | Stella et al. | 514/291 |
| 4,885,171 | 12/1989 | Sehgal et al. | 424/122 |
| 5,023,263 | 6/1991 | Von Burg | 514/291 |
| 5,023,264 | 6/1991 | Caufield et al. | 514/291 |
| 5,100,899 | 3/1992 | Calne | 514/291 |

FOREIGN PATENT DOCUMENTS 0413532  2/1991  European Pat. Off. ............ 546/90

OTHER PUBLICATIONS

J. Antibiot. 28, 721–726 (1975).
J. Antibiot. 28, 727–732 (1975).
J. Antibiot. 31, 539–545 (1975).
Can. J. Physiol. Pharmacol. 55, 48 (1977).
FASEB 3,3411 (1989).
FASEB 3,5256 (1989).
Lancet 1183 (1978).
Med. Sci. Res. 17: 877 (1989).

Primary Examiner—Elli Peselev
Attorney, Agent, or Firm—Arnold S. Milowsky

[57] ABSTRACT

This invention provides metabolites of rapamycin, the first of which is 41-O-desmethyl rapamycin, having a deprotonated molecular ion detected at a mass to charge ratio of 899, and a characteristic desorption chemical ionization mass spectroscopic fragmentation pattern comprising ions detected at a mass to charge ratio of 591, 569, 559, 543, 529, 421, and 308. A second compound of this invention is a hydroxylated metabolite of rapamycin having a deprotonated molecular ion detected at a mass to charge ratio of 928, and a characteristic direct chemical ionization mass spectroscopic fragmentation pattern comprising ions detected at a mass to charge ratio of 607, 571, 545, 513, 322, 290, and 241 amu. The compounds of this invention, by virtue of their immunosuppressive activity are useful in treating transplantation rejection, host vs. graft disease, autoimmune diseases and diseases of inflammation; by virtue of their antitumor activity are useful in treating solid tumors; and by virtue of their antifungal activity are useful in treating fungal infections.

8 Claims, No Drawings

RAPAMYCIN METABOLITES

BACKGROUND OF THE INVENTION

This invention relates to metabolites of rapamycin and a method for using them in the treatment of transplantation rejection, host vs. graft disease, autoimmune diseases, diseases of inflammation, solid tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

The compounds of this invention are metabolites of rapamycin that are useful as immunosuppressive, antiinflammatory, antifungal, and antitumor agents. The first compound of this invention is a metabolite identified as 41-O-desmethyl rapamycin, having a deprotonated molecular ion detected at a mass to charge ratio of 899, and a characteristic desorption chemical ionization (DCI) mass spectroscopic fragmentation pattern comprising ions detected at a mass to charge ratio of 591, 569, 559, 543, 529, 421, and 308. A second compound of this invention is a hydroxylated metabolite of rapamycin having a deprotonated molecular ion detected at a mass to charge ratio of 928, and a characteristic DCI mass spectroscopic fragmentation pattern comprising ions detected at a mass to charge ratio of 607, 571, 545, 513, 322, 290, and 241.

The compounds of this invention can be prepared by reacting rapamycin in an in vitro human liver microsome preparation, which is a standard pharmaceutical test procedure that emulates hepatic metabolism in humans. Alternatively, the compounds of this invention can be prepared by reacting rapamycin in an in vitro intestinal microsome preparation, which is a standard pharmacological test procedure that emulates intestinal metabolism in humans. It is contemplated that the compounds of this invention can also be produced by other standard metabolic test procedures that emulate mammalian metabolism. It is further contemplated that the compounds of this invention can be prepared using synthetic organic chemical methodology.

The compounds of this invention can be separated from the microsomal preparation by solid/liquid extraction onto a reversed phase chromatography column, and subsequent elution, with a suitable solvent, such as dichloromethane, and can be separated from any unreacted rapamycin and other metabolites using standard purification techniques, such as reverse phase column chromatography. Other methods of extraction and purification will be apparent to one skilled in the art.

The structural elucidation for the compounds of this invention can be accomplished using standard spectroscopic techniques such as mass spectroscopy, nuclear magnetic resonance, infrared spectroscopy, ultraviolet spectroscopy, and the like. In addition, the compounds of this invention can be characterized by their retention times using HPLC. Other methods of characterization and structural analysis will be apparent to one skilled in the art.

Immunosuppressive activity of the collected fractions was evaluated in an in vitro standard pharmacological test procedure designed to measure lymphocyte proliferation. The procedure used is briefly described below.

Human lymphocytes were isolated from blood anticoagulated with heparin. Blood was centrifuged with ficoll at 545 g at room temperature for 20 min. The lymphocyte layer was washed with phosphate buffered saline by centrifugation at 280 g for 10 min and subsequently with the culture medium (430 g, 10 min). The cells were adjusted to a concentration of $10^6$ cells/mL with RPMI 1640 medium supplemented with 2 mM glutamine, 100 U/mL penicillin, 100 μg streptomycin and 10% fetal calf serum. For each fraction evaluated, the 1 g/L solution in methanol was diluted with culture medium to provide a concentration of 1 mg/L. The concentration of metabolite in each fraction was determined by HPLC comparison with an external rapamycin standard curve. A solution composed of 100 μL of the cell suspension, containing 5 mg/L PHA, and 100 μL of the metabolite solution were pipetted into the wells of a 96-well plate. The cells were incubated for 44 h at 37° C. in a 5% $CO_2$ atmosphere. After addition of 1 μCi $^3$H-thymidine/well the cells were incubated for additional 4.5 h. Incubation was terminated by deep freezing. The thawed cells were harvested and $^3$H-thymidine incorporation was determined by liquid scintillation counting.

The following table shows the results obtained for the compounds of this invention.

| Compound | $IC_{50}$ (nmol/L) |
|---|---|
| Example 1 | 1.0 |
| Example 2 | 1.5 |
| Rapamycin | 0.1 |

The results of this standard pharmacological test procedure demonstrate that the compounds of this invention are useful as immunosuppressive agents. Because the compounds of this invention are structurally similar to rapamycin and have a similar activity profile to rapamycin, the compounds of this invention also are considered to have antifungal, and antitumor activity.

Based on the results of these standard pharmacological test procedures, the compounds of this invention are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease, and eye uveitis; solid tumors; and fungal infections.

The compounds of this invention may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions an be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1–5 percent, preferably 2%, of active compound which may be administered to a fungally affected area.

The following examples illustrate the preparation of the compounds of this invention.

EXAMPLE 1

41-O-Desmethyl rapamycin

Human liver microsomes were isolated using standard centrifugation techniques using phosphate buffer at pH 7.4. [F. P. Guengerich, Principles and Methods of Toxicology, A. W. Hayes, ed., 609 (1982)]. The protein concentration was determined according to the method of Lowry [J. Biol. Chem. 193: 265 (1951)] and the cytochrome P450 concentration was determined according to the method of Omura [J. Biol. Chem. 239: 2370 (1964)]. Following isolation, the protein concentration was adjusted to 0.75 mg/mL.

A stock solution of rapamycin was prepared in acetonitrile/water (pH 3.0) 75/25 v/v at a concentration of 1 mM. Twenty-five (25) µL of this solution were added to 1 mL of the microsomal preparation. The reaction was started by adding 0.5 mL of an NADPH regenerating system consisting of 2 mM EDTA, 10 mM $MgCl_2$, 0.84 mM NADP, 18 mM isocitric acid, and 667 U/L isocitrate dehydrogenase dissolved in 0.1 mM phosphate buffer at pH 7.4. The microsomal preparation was incubated at 37° C. for 11 min for isolation of the metabolites from the microsomal preparation and the reaction was terminated by protein precipitation with 0.5 mL acetonitrile.

Following protein precipitation, the mixture was centrifuged at 2500 g for 2 min and the supernatant was loaded on a 3 mL solid/liquid extraction column filled with reversed phase $C_8$ material that had previously been eluted with a mixture of acetonitrile and water adjusted to pH 3.0. The columns were subsequently washed with 3 mL of methanol/water 50/50 v/v at pH 3.0 and 1 mL hexane. The column was air dried for 5 min by pulling a vacuum on the non-loaded end of the column and placed in a diethyl ether washed 10 mL centrifuge tube. The mixture of metabolized and unmetabolized rapamycin was eluted by centrifuging 2 mL of dichloromethane through the extraction column (800 g, 2 min).

Eighty (80) samples had to be extracted as described above to provide sufficient material for separation by semi-prepartative HPLC. The combined eluants were evaporated under a stream of nitrogen to provide a residue that was dissolved in 2 mL acetonitrile/water pH 3.0 75/25 v/v and loaded on two subsequently linked 250×10 mm columns, filled with 10 µM, $C_8$ Nucleosil®. The columns were eluted at a flow rate of 5 mL/min with the following water (adjusted to pH 3 with sulfuric acid) and acetonitrile gradient: analysis time 0 min: 47% acetonitrile, 7 min: 47% acetonitrile, 20 min: 50% acetonitrile, 40 min: 55% acetonitrile, 45 min: 61% acetonitrile. A column temperature of 75° C. was maintained and the UV detector was set to a wavelength of 276 nm. Fractions were collected based on a positive absorbance at 276 nm. The isolated fractions were diluted with an equal volume of water (pH 3.0) and adsorbed onto a 3 mL solid/liquid extraction column filled with reversed phase $C_8$ material that had previously been eluted with a mixture of acetonitrile and water adjusted to pH 3.0. The column was eluted by centrifuging 2 mL dichloromethane through the extraction column (800 g, 2 min). The eluant was evaporated and the residue was dissolved in methanol at a concentration of 1 g/L and stored at −18° C. Physical characterization and structural analysis of the components of the collected were accomplished by analytical HPLC, and mass spectroscopy, respectively; the procedures used and results obtained are provided below.

Analytical HPLC was conducted by eluting samples through a 250×4 mm analytical column subsequently linked to a 100×4 mm analytical column. Both columns were filled with 3 µm, $C_8$ Nucleosil®. A 30×4 mm precolumn filled with 5 µM, $C_8$ Nucleosil® was used as a column guard. The columns were eluted at a flow rate of 5 mL/min with the following water (adjusted to pH 3 with sulfuric acid) and acetonitrile gradient: analysis time 0 min: 47% acetonitrile, 7 min: 47% acetonitrile, 20 min: 50% acetonitrile, 40 min: 55% acetonitrile, 45 min: 61% acetonitrile. A column temperature of 75° C. was maintained and the UV detector was set to a wavelength of 276 nm. The title compound had a retention time of 29.7 min.

The compound was analyzed by negative ion fast atom bombardment (FAB) mass spectroscopy and DCI mass spectrometry. The fragmentation pattern of the title compound was compared with those obtained for rapamycin for structural elucidation purposes. FAB mass spectrometry was conducted using sample sizes of 2–3 µg with glycerine as a matrix, xenon as the bombardment gas, and the primary beam energy in the FAB source was 8 kV. Isobutane was the reagent gas for DCI mass spectrometry. The following mass spectral data were obtained for the title compound. In the negative ion FAB mass spectrum, the deprotonated molecular ion was observed at a mass to charge ratio of 899 which represents the loss of a methyl group from rapamycin, the position of which was assigned based on the DCI fragmentation pattern.

MS (neg. ion FAB, m/z): 899 [M−H]⁻;

MS (neg. ion DCI, m/z): 591, 569, 559, 543, 541, 529, 497, 421, 407, 390, 374, 336, 322, 308, 290, 252, 241, 234, 222, 206, 168, and 151.

EXAMPLE 2

A hydroxylated metabolite of rapamycin

The title compound was prepared following the method described in Example 1. Physical characterization and structural analysis of the components of the collected were accomplished by analytical HPLC, and mass spectroscopy, respectively under the conditions that were described above. The title compound had a retention in the above described HPLC system of 22.5 min. The deprotonated molecular ion detected at a mass to charge ratio of 928 represents a hydroxylation product of rapamycin.

MS (neg. ion FAB, m/z):928 [M−H]⁻;

MS (neg. ion DCI, m/z): 607, 589, 587, 571, 569, 557, 545, 513, 402, 390, 322, 308, 304, 290, 264, 250, 241, 222, 220, 208, 197, 156, 151, 139, and 111.

EXAMPLE 3

In vitro metabolism by rat intestinal microsomes

The compounds of this invention can be prepared by the metabolism of rapamycin in a standard pharmacological test procedure using rat small intestinal microsomes. The following briefly exemplifies the procedure used. Small intestinal microsomes were obtained from male Sprague-Dawley rats. Two days before the animals were sacrificed, the cytochrome P450 system was induced by the administration of a single 80 mg/kg interperitoneal dose of dexamethasone. Rat enterocytes were isolated according to the method of Pinkus and Porteous [Methods Enzymol 77: 154 (1981); Biochem J 180: 455 (1979)]. Microsomes were obtained from the enterocytes as described for human liver microsomes. The protein concentration was adjusted to 270 µg/mL and 25 µL of a rapamycin solution (1 mM in acetonitrile/water pH 3.0, 75/25 v/v) were incubated with the microsomes for 40 minutes as described above. The compounds of this invention are isolated and purified following this procedure as described in Example 1.

What is claimed is:

1. A compound which is 41-O-desmethyl rapamycin.

2. A hydroxylated metabolite of rapamycin having a deprotonated molecular ion detected at a mass to charge ratio of 928, and a characteristic desorption chemical ionization mass spectroscopic fragmentation pattern comprising ions detected at a mass to charge ratio of 607, 571, 545, 513, 322, 290, and 241.

3. A method of inducing immunosuppression in a mammal in need thereof, which comprises administering an effective amount 41-O-desmethyl rapamycin.

4. A method of inducing immunosuppression in a mammal in need thereof, which comprises administering an effective amount of a hydroxylated metabolite of rapamycin having a deprotonated molecular ion detected at a mass to charge ratio of 928, and a characteristic desorption chemical ionization mass spectroscopic fragmentation pattern comprising ions detected at a mass to charge ratio of 607, 571, 545, 523, 322, 290, and 241.

5. The method according to claim 3, wherein immunosuppression is induced to treat a disorder selected from the group consisting of transplantation rejection, host vs. graft disease and auto-immune diseases.

6. The method according to claim 4, wherein immunosuppression is induced to treat a disorder selected from the group consisting of transplantation rejection, host vs. graft disease and auto-immune diseases.

7. A method of treating diseases of inflammation in a mammal in need thereof, which comprises administering an effective amount 41-O-desmethyl rapamycin.

8. A method of treating diseases of inflammation in a mammal in need thereof, which comprises administering an effective amount of a hydroxylated metabolite of rapamycin having a deprotonated molecular ion detected at a mass to charge ratio of 928, and a characteristic desorption chemical ionization mass spectroscopic fragmentation pattern comprising ions detected at a mass to charge ratio of 607, 571, 545, 513, 322, 290, and 241.

* * * * *